US00PP09935P

United States Patent [19]

Wain

[11] Patent Number: Plant 9,935

[45] Date of Patent: Jun. 24, 1997

[54] CHRYSANTHEMUM PLANT NAMED 'FASHION TIME'

[75] Inventor: Peter Wain, Hants, United Kingdom

[73] Assignee: Cleangro Ltd., Chicester, United Kingdom

[21] Appl. No.: 627,606

[22] Filed: Apr. 4, 1996

[51] Int. Cl.[6] ..... A01H 5/00

[52] U.S. Cl. ..... Plt./80

[58] Field of Search ..... Plt./76, 80

*Primary Examiner*—Howard J. Locker

*Attorney, Agent, or Firm*—C. A. Whealy

[57] ABSTRACT

A distinct cultivar of Chrysanthemum plant named Fashion Time, characterized by its flat capitulum form; vigorous and tall growth habit; freely branching plant habit; medium decorative-type inflorescences; medium pink ray florets; numerous inflorescences per plant; numerous ray florets per inflorescence; and good postproduction longevity.

1 Drawing Sheet

The present invention relates to a new and distinct cultivar of Chrysanthemum plant, botanically known as *Dendranthema grandiflora* and referred to by the cultivar name Fashion Time.

The new cultivar is a product of a planned breeding program conducted by the inventor in Havant, Hampshire, United Kingdom. The objective of the breeding program was to create new Chrysanthemum cultivars having a fast flowering response, desirable inflorescence colors, and inflorescences and foliage with good substance.

The new cultivar originated from a cross made by the inventor of the inventor's proprietary Chrysanthemum selection No. P7–88 as the male or pollen parent with the inventor's proprietary Chrysanthemum selection No. P33–88 as the female or seed parent.

The cultivar Fashion Time was discovered and selected by the inventor as a flowering plant within the progeny of the stated cross in a controlled environment in Havant, Hampshire, United Kingdom.

Asexual reproduction of the new cultivar by terminal cuttings taken at Havant, Hampshire, United Kingdom, has shown that the unique features of this new Chrysanthemum are stable and reproduced true to type in successive generations.

The following traits have been repeatedly observed and are determined to be the unique characteristics of Fashion Time. These characteristics in combination distinguish Fashion Time as a new and distinct cultivar:

1. Flat capitulum form.
2. Vigorous and tall growth habit.
3. Freely branching plant habit.
4. Medium decorative-type inflorescences.
5. Medium pink ray florets.
6. Numerous inflorescences per plant.
7. Numerous ray florets per inflorescence.
8. Good postproduction longevity with inflorescences maintaining good substance and color for more than 18 days in an interior environment.

The cultivar Fashion Time has not been observed under all possible environmental conditions. The phenotype may vary somewhat with variations in environment such as temperature, daylength and light intensity, without, however, any variance in genotype.

In side-by-side comparisons in Havant, Hampshire, United Kingdom, under commercial practice, plants of the new Chrysanthemum have larger inflorescences that are lighter pink in color compared to plants of the male parent, the proprietary selection P7–88. In the same comparisons, plants of the new Chrysanthemum have larger inflorescences that are darker pink in color and more florets per inflorescence than plants of the female parent, the proprietary selection P33-88.

Plants of the new Chrysanthemum are similar to the cultivar Wain's Pink Lady (disclosed in U.S. Plant Pat. No. 8,573) in ray floret color. However, in side-by-side comparisons conducted in Oxnard, Calif., under commercial practice, plants of the new Chrysanthemum differed from plants of the cultivar Wain's Pink Lady in the following characteristics:

1. Plants of the new Chrysanthemum are more freely branching and more vigorous than plants of the cultivar Wain's Pink Lady.
2. Leaves of plants of the new Chrysanthemum are larger than leaves of plants of the cultivar Wain's Pink Lady.
3. Ray florets of plants of the new Chrysanthemum are slightly lighter in color than ray florets of plants of the cultivar Wain's Pink Lady.
4. Plants of the new Chrysanthemum have more ray florets per inflorescence than plants of the cultivar Wain's Pink Lady.
5. The peduncle angle of plants of the new Chrysanthemum is more acute than the peduncle angle of plants of the cultivar Wain's Pink Lady.

A detailed comparison of plants of the new Chrysanthemum and the cultivar Wain's Pink Lady appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Fashion Time with five cuttings in the container and the terminal inflorescences removed (center-budded pot chrysanthemum).

In the following description, color references are made to The Royal Horticultural Society Colour Chart except where general terms of ordinary dictionary significance are used. The following observations and measurments describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 21 long day/short nights followed by short day/long nights until flowering. Two weeks after the start of the short day/long night treatment, plants received four weekly spray applications of daminozide growth retardant at a rate of 2,500 ppm. Measurments and numerical values represent ranges or averages for six typical flowering plants.

Botanical classification: *Dendranthema grandiflora* cultivar Fashion Time.

Commercial classification: Decorative potted chrysanthemum.

Parentage:

*Male, or pollen, parent.*—Proprietary selection P7-88.

*Female, or seed, parent.*—Proprietary selection P33-88.

Propagation:

*Type.*—Terminal tip cuttings.

*Time to rooting.*—7 to 10 days with soil temperatures of 21° C.

*Rooting habit.*—Fine, fibrous and well-branched.

Plant description:

*Appearance.*—Perennial herbaceous decorative potted plant. Stems upright, uniform habit and freely branching. Vigorous and tall growth habit.

*Plant height.*—27.5 to 28 cm.

*Lateral branch length.*—19.5 to 22.5 cm.

*Quantity of lateral branches after removal of apical meristem.*—About 3.5.

*Stem color.*—147B.

*Foliage description.*—Number of leaves per lateral branch: 15 to 17. Leaf arrangement: Alternate. Leaf size, fully expanded: Length: 10.5 to 11.5 cm. Width: 6 to 7 cm. Leaf apex: Acuminate. Leaf base: Attenuate. Leaf margin: Palmately lobed. Leaf texture: Upper and under surfaces slightly pubescent, smooth and dull. Veins prominent on under surface. Petiole length: About 2 cm. Color: Young foliage upper surface: 147A. Young foliage under surface: 147B. Fully expanded foliage upper surface: 147A. Fully expaned foliage under surface: 147B. Venation upper surface: 147B. Venation under surface: 147B. Petiole: 147A.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 57 to 59 days later.

*Postproduction longevity.*—In an interior environment, inflorescences and foliage of flowering plants will maintain good color and substance for at least 2 weeks in an interior environment.

*Quantity of inflorescences.*—7 to 8 inflorescences per flowering stem.

*Inflorescence size.*—Diameter: 9.5 to 10 cm. Depth (height): About 3.1 cm. Diameter of disc: About 3 mm.

*Ray florets.*—Shape: Long, broad. Size: Length: 4.5 to 4.8 cm. Width: 1.4 to 1.6 cm. Apex: Rounded. Base: Acute. Margin: Entire. Texture: Satiny, smooth and glabrous. Aspect: Flat. Number of ray florets per inflorescence: About 350. Color: When opening, upper surface: 62B. When opening, under surface: 62B. Mature, upper surface: 62C, fading to 155D with subsequent development. Mature, under surface: 62D.

*Disc florets.*—Shape: Tubular. Size: Length: About 4 mm. Width: About 1 mm. Number of disc florets per inflorescence: About 10. Color: Immature: 154A. Mature: 12A.

*Peduncle.*—Aspect: Strong and angled about 25° to the stem. Length: 5.5 to 6 cm. Texture: Glabrous. Color: 147B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

CHART A

| CHARACTERISTIC | FASHION TIME | WAIN'S PINK LADY |
|---|---|---|
| QUANTITY OF LATERAL BRANCHES AFTER REMOVAL OF TERMINAL APEX | About 3.5 | About 3 |
| VIGOR | Vigorous | Moderate |
| LEAF LENGTH | 10.5 to 11.5 cm | 7 to 8 cm |
| LEAF WIDTH | 6.5 to 7 cm | 4.5 to 5.5 cm |
| RAY FLORET COLOR, WHEN OPENING, UPPER SIDE | 62B | 70B |
| RAY FLORET COLOR, MATURE, UPPER SIDE | 62C | 62B |
| RAY FLORET COLOR, MATURE, UNDER SIDE | 62D | 62C |
| NUMBER OF RAY FLORETS PER INFLORESCENCE | About 350 | About 183 |
| DISC FLORET LENGTH | About 4 mm | About 3 mm |
| DIAMETER OF DISC | About 3 mm | About 2 mm |
| PEDUNCLE ANGLE | About 25° | About 40° |

It is claimed:

1. A new and distinct cultivar of Chrysanthemum plant named Fashion Time, as illustrated and described.

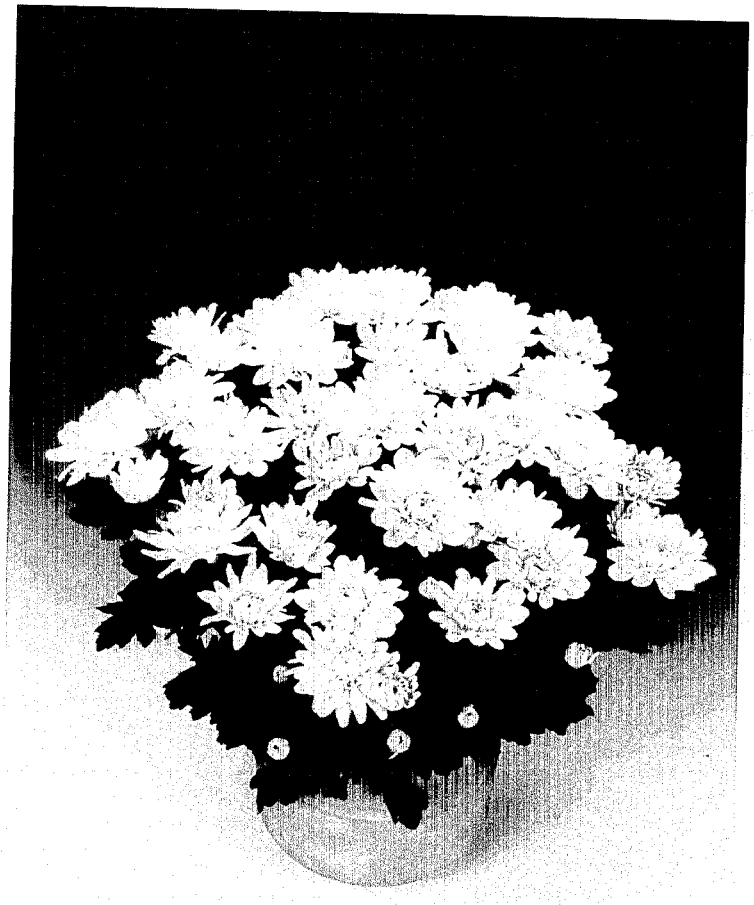

* * * * *